United States Patent [19]

Santos

[11] Patent Number: 4,635,634
[45] Date of Patent: Jan. 13, 1987

[54] SURGICAL CLIP APPLICATOR SYSTEM

[76] Inventor: Manuel V. Santos, 126 Pulaski St., Newark, N.J. 07105

[21] Appl. No.: 754,651

[22] Filed: Jul. 12, 1985

[51] Int. Cl.$^4$ .............................................. A61B 17/12
[52] U.S. Cl. .................................... 128/325; 128/326; 72/410; 227/DIG. 1
[58] Field of Search ........................ 128/325, 326, 321; 72/410; 227/DIG. 1 R, DIG. 1 S, DIG. 1 M, DIG. 1 C

[56] References Cited

U.S. PATENT DOCUMENTS

| | | | |
|---|---|---|---|
| 2,910,067 | 10/1959 | White | 128/334 R |
| 3,777,538 | 12/1973 | Weatherly et al. | 128/325 |
| 3,828,791 | 8/1974 | Santos | 128/321 |
| 3,856,016 | 12/1974 | Davis | 128/325 |
| 3,867,944 | 2/1975 | Samuels | 128/321 |
| 3,906,957 | 9/1975 | Weston | 128/321 |
| 3,945,238 | 3/1976 | Eckert | 227/DIG. 1 C |
| 3,954,108 | 5/1976 | Davis | 128/321 |
| 4,027,510 | 6/1977 | Hiltebrant | 128/325 |
| 4,152,920 | 5/1979 | Green | 128/325 |
| 4,242,902 | 1/1981 | Green | 128/325 |
| 4,263,903 | 4/1981 | Griggs | 128/92 B |
| 4,273,129 | 6/1981 | Boebel | 227/DIG. 1 C |
| 4,296,881 | 10/1981 | Lee | 128/334 R |
| 4,316,468 | 2/1982 | Klieman et al. | 128/325 |
| 4,325,376 | 4/1982 | Klieman et al. | 128/325 |
| 4,354,628 | 10/1982 | Green | 128/334 R |
| 4,394,864 | 7/1983 | Sandhaus | 128/321 |
| 4,396,139 | 8/1983 | Hall et al. | 227/19 |
| 4,402,445 | 9/1983 | Green | 128/334 R |
| 4,412,539 | 11/1983 | Jarvik | 128/325 |
| 4,440,170 | 4/1984 | Golden et al. | 128/325 |
| 4,471,780 | 9/1984 | Menges et al. | 128/326 |

FOREIGN PATENT DOCUMENTS 2553540  6/1977  Fed. Rep. of Germany ...... 128/326

*Primary Examiner*—Robert Peshock
*Assistant Examiner*—Cary E. Stone
*Attorney, Agent, or Firm*—R. Martin Oliveras

[57] ABSTRACT

A surgical clip applicator system for receiving a clip from a clip holder and for compressively applying the clip to a body vessel or tissue comprises a stationary front jaw member, a rotatable rear jaw member, and rear jaw member actuator. The stationary front jaw member includes a rear facing grooved surface and a rear facing depressed notch above the grooved surface which further includes a rearward projection along the upper part of the notch. The rotatable rear jaw member includes a front facing grooved surface, a front facing depressed notch above the grooved surface which further includes a frontward projection along the upper part of the notch, a first location wherein the actuator is rotatably connected to the rear jaw member, and a second location wherein the rear jaw member is rotatably connected to the front jaw member. The V-shaped open clip is manually snapped onto the clip holder and is thereafter snapped onto the front and rear facing grooved surfaces of the surgical clip applicator for preventing lateral motion of the open clip and wherein the frontward and rearward projections prevent upward movement of the open clip. The actuator causes forward rotation of the rear jaw member onto the jaw member thereby compressing the clip onto the vessel or tissue. The actuating member includes spring means to cause separation of the jaw members to release the compressed clip around the vessel or tissue from the surgical clip applicator.

5 Claims, 8 Drawing Figures

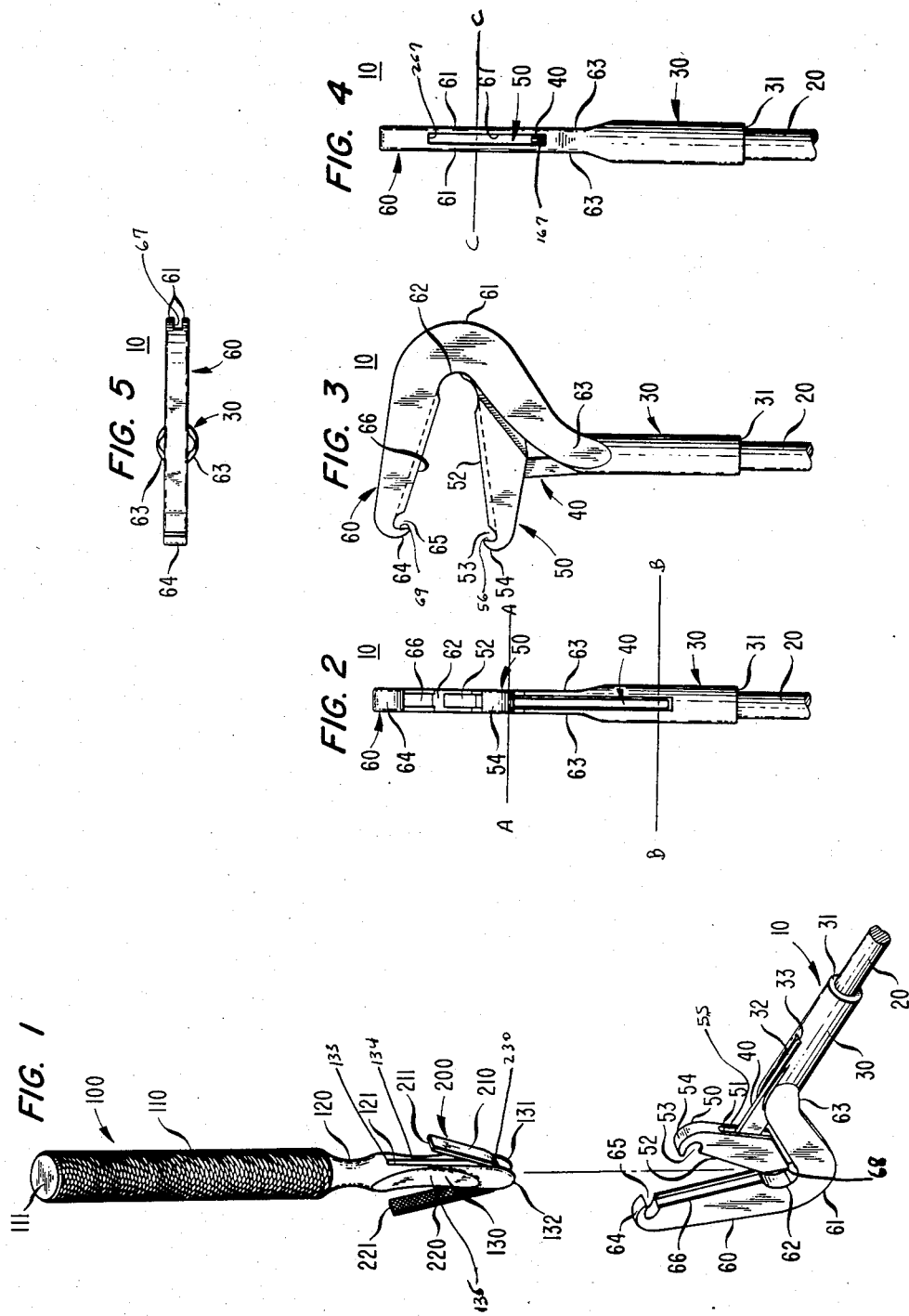

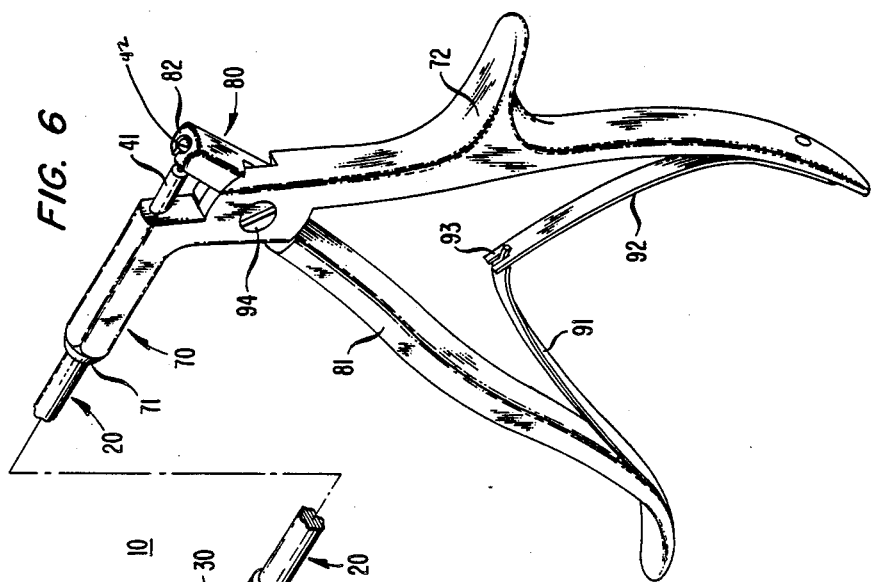
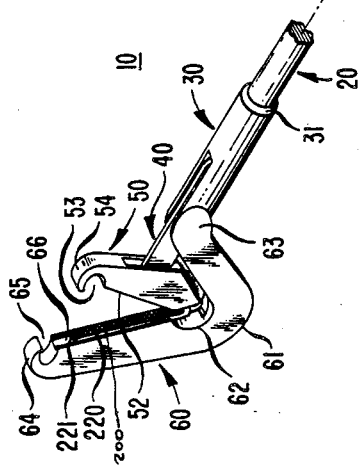
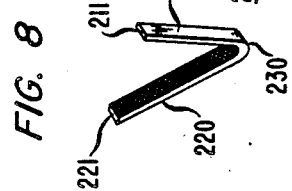
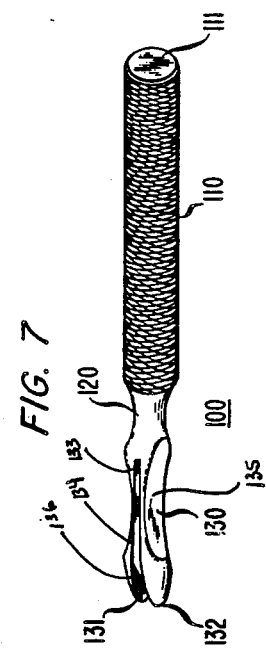

SURGICAL CLIP APPLICATOR SYSTEM

FIELD OF THE INVENTION

This invention relates to blood vessel tissue occlusion means and in particular to a surgical dip applicator system comprising a clip, a clip holder, and a surgical clip applicator.

OTHER RELATED APPLICATIONS

This utility patent application is related to design patent application Ser. No. 680312 entitled "Thermoclip Applicator" and filed on 12/10/84 by the same inventor herein.

DISCUSSION OF THE PRIOR ART

The prior art discloses several surgical clip applicators as follows:

White U.S. Pat. No. 2,910,067 discloses a wound clip comprising a strip of thin deformable material having enlarged jaw engaging ends, a rearwardly bowed central portion, and flesh engaging prongs. Specifically disclosed are clips 31, rack means 50, and extraction tool 60;

Weatherly et al U.S. Pat. No. 3,777,538 discloses a surgical clip applicator comprising a handle member, a housing, a trigger member, biasing means, an elongated tubular barrel, a rod, and Jaws. Specifically disclosed are surgical clip applicator 11 and clip 62;

Santos U.S. Pat. No. 3,828,791 discloses a surgical instrument comprising a handle having two handle parts, interconnecting means, a rod, a tube, and two jaws. Specifically disclosed are surgical instrument 20 with jaws 19 and 23;

Davis U.S. Pat. No. 3,856,016 discloses a method for applying an occlusion clip comprising the steps of securely mounting an occlusion clip onto a tubular instrument, inserting the end of the tubular instrument through an opening in an anatomical body, optically positioning the open jaws and the clip mounted thereon in a proper position, and clamping the clip to produce an occlusion in the anatomical structure. Specifically disclosed are occlusion clip blank 10, fixed jaw 34, light source 64, jaw 32, and tubular member 50;

Samuels U.S. Pat. No. 3,867,944 discloses a hemostatic clip formed of an elongate, substantially flat strip defining a generally V-shaped clip. Specifically disclosed are hemostatic clip 10 and the hemostatic clip applicator of FIG. 1;

Davis U.S. Pat. No. 3,954,108 discloses an instrument for applying an occlusion clip, which clip is composed of bendable material, said instrument comprising a tubular housing, jaw means, and actuating means. Specifically disclosed are occlusion clip blank 10, jaws 32 and 34, tubular structure 50, and light beam 61;

Hiltebrandt U.S. Pat. No. 4,027,510 discloses a forceps instrument comprising an outer sleeve member, a guiding viewing tube support, a tubular barrel, optical viewing means, a pair of pivotally mounted opposing jaws, locking means, and hand operated jaw actuation means. Specifically disclosed are jaws 3 and 4, tubular barrel 1, and clip 31;

Green U.S. Pat. No. 4,152,920 discloses a system for applying surgical clips comprising an instrument and a disposable cartridge, the disposable cartridge having elongated blade means, actuation means, and cartridge housing means; and the instrument comprising a body and driver means. Specifically disclosed are instrument 10 and detachably mounted disposable cartridge 12;

Green U.S. Pat. No. 4,242,902 discloses an apparatus for applying surgical clips comprising a pair of opposed spaced apart grooved jaws, means adapted to contain a plurality of surgical clips, and means operable to close the jaws. Specifically disclosed are instrument assembly 10, detachably mounted disposable cartridge 12, and clips 200;

Griggs U.S. Pat. No. 4,263,903 discloses a medical staple for being held by a staple holder and including a first leg member, a second leg member, a bridge member, and groove means on the bridge member. Specifically disclosed are medical staple 11 and medical staple holder 13;

Lee U.S. Pat. No. 4,296,881 discloses a surgical stapling tool using disposable cartridge elements and having staple folding anvil, an actuator, a holder, and a pusher. Specifically disclosed are tool 10 and staple holder 22;

Klieman et al U.S. Pat. No. 4,316,468 discloses a surgical clip applying device comprising a main body, a clip magazine, clip loading means, clip deforming means, clip feed means, and actuating means. Specifically disclosed are hemostatic clip applying device 2 and clips 37;

Klieman et al U.S. Pat. No. 4,325,376 discloses a surgical clip applyi device comprising a main baody, a clip magazine, clip deforming means, laminated clip feed means, and actuating means. Specifically disclosed are hemostatic clip applying device 2 and hemostatic clips 37;

Green U.S. Pat. No. 4,354,628 discloses a surgical staple cartridge for use with an actuator assembly including a rigid frame having a U-shaped portion for forming a plurality of surgical staples comprising an anvil member, a staple holder, and means for allowing the cartridge to be removably mounted on the actuator frame. Specifically disclosed are instrument 10 and staple holder portion 60;

Sandhaus U.S. Pat. No. 4,394,864 discloses an apparatus for effecting occlusion of a vessel comprising a locking clip delivering instrument, means for movably mounting the U-shaped locking clip, means for actuating the jaw members, means for actuating the U-shaped locking clip, and means for actuating the jaw members from the closed position to the open position. Specifically disclosed are apparatus 10 and U-shaped locking clip 30;

Hall et al U.S. Pat. No. 4,396,139 discloses a stapling device comprising a housing, a handle, a trigger, a magazine control means. Specifically disclosed are stapler 10 and staples 21;

Green U.S. Pat. No. 4,402,445 discloses a surgical fastener comprising a fastener member and a retainer member. Specifically disclosed are actuator assembly 12, fastener applying cartridge 14, and retainer member 80;

Jarvik U.S. Pat. No. 4,412,539 discloses a repeating instrument for applying surgical clips comprising an elongated main body portion, first and second opposed jaws, an elongated channel, pusher means, first and second lever arms, biasing means, pusher sequencing means, and jaw sequencing means. Specifically disclosed are hemostatic clip applying means 42 and clips 136;

Golden et al U.S. Pat. No. 4,440,170 discloses a surgical clip applicator comprising a handle member, a pair of spaced apart cradles, a trigger member, an elongated tubular assembly, means engaging the trigger member, means restraining the rod member, means aligning the jaws, and means for rotating the mounted tubular jaw assembly. Specifically disclosed are tube 14, jaw 15, rod 16, jaw 17, and clip 17; and Menges et al U.S. Pat. No. 4,471,780 discloses a medical instrument for applying ligating clips in succession comprising a scissors type handle including a main handle body, a movable jaw assembly, a feeding mechanism, a first transmission mechanism, and a second transmission mechanism. Specifically disclosed are handle 10, cartridge 12, and clips 11.

While there are numerous clips and applicators for same known in the prior art, they do not appear to reveal the surgical clip applicator system of the present invention comprising the clip, the clip holder, and the surgical clip applicator.

The main object of the present invention is therefor to provide the aforementioned clip applicator system with all its advantages and features.

SUMMARY AND FEATURES OF THE PRESENT INVENTION

The present invention is described as follows and has the following features:

the V-shaped clip comprises first and second flat straight extensions and an interconnecting curved section;

the clip holder comprises: a first end for manually holding the clip holder; and a second end including first and second extensions defining a longitudinal slit of decreasing width therebetweeen, such extensions each including a step on the medial surfaces thereof for manually snapping on the open clip and for securely holding the open clip along the lateral edges of the intermediate curved section;

the surgical clip applicator comprises: a stationary front jaw member including a rear facing grooved surface and a rear facing depressed notch above the grooved surface, the notch being defined above by a rearward projection; a rotatable rear jaw member including a front facing grooved surface and a front facing depressed notch above the grooved surface, the notch being defined above by a frontward projection; rear jaw member actuating means for causing rotation of the rear jaw member relative to the front jaw member, the front jaw member having attached thereto a hollow tubular structure which in turn has attached thereto a fixed rear handle; the actuating means including a first member being rotatably attached to the rear jaw member and which has both displacement and rotation, an internal rod member being located within the hollow tubular structure, and a rotatable rear handle;

the clip holder is utilized to snap the open clip onto the surgical clip applicator such that the clip extensions fall into the jaw member grooved surfaces to prevent lateral motion of the open clip and such that the clip extension ends fall into the jaw member depressed notches below the projections to prevent upward motion of the open clip;

the actuating means causes forward rotation of the rear jaw member relative to the front jaw member, the clip is compressed onto the subject vessel or tissue, then spring means associated with the actuating means causes the rear jaw member to rotate away from the front jaw member to release the compressed or closed clip and the vessel or tissue from the surgical clip applicator;

the angle between the open clip extensions is about 23 degrees;

the angle between the jaw member grooved surfaces in the open configuration of the surgical clip applicator is also about 23 degrees;

the angle between the front jaw member grooved surface and the longitudinal axis of the hollow tubular structure is about 73 degrees;

the angle between the rear jaw member grooved surface and the longitudinal axis of the hollow tubular structure in the open configuration is about 96 degrees;

the angle between the closed clip extensions and the longitudinal axis of the hollow tubular structure in the closed configuration is about 73 degrees;

the angle between the rear jaw member grooved surface and the longitudinal axis of the hollow tubular member in the closed configuration is about 73 degrees; and the angles between the open clip extensions and the longitudinal axis of the hollow tubular structure in the open configuration are about 73 degrees and 96 degrees.

Advantages of the present invention are therefor that:
it allows for clip closing control with visibility;
the clip provides good reliable holding power;
the surgical clip applicator system is simple in construction, reliable in operation, easy to handle, and inexpensive to manufacture; and
the surgical clip applicator securely holds the open clip prior to closing same onto the vessel or tissue.

DESCRIPTION OF THE DRAWING

The above and other objects, features, and advantages of the present invention will be better appreciated from a reading of the following detailed description with reference to the drawing in which:

FIG. 1 is a perspective view of the surgical clip applicator system of the present invention including the surgical clip applicator front end, the clip holder, and the clip;

FIG. 2 is a top view of the front end of the surgical clip applicator;

FIG. 3 is a lateral view of the front end of the surgical clip applicator;

FIG. 4 is a bottom view of the front end of the surgical clip applicator;

FIG. 5 is a front view of the front end of the surgical clip applicator;

FIG. 6 is a perspective view of the complete surgical clip applicator;

FIG. 7 is a perspective view of the clip holder; and

FIG. 8 is a perspective view of the clip.

DETAILED DESCRIPTION

FIG. 1 is a perspective view of the surgical clip applicator system of the present invention showing the front end of surgical clip applicator 10 in the open configuration, clip holder 100, and clip 200 in the open configuration.

Surgical clip applicator 10 comprises: intermediate external hollow tubular member 20; front external hollow tubular member 30; actuating member 40; rear rotatable jaw member 50; and front stationary jaw member 60. Longitudinally directed members 20 and 30 are fixedly connected to each other at location 31. Member 30 includes a longitudinally directed slot being defined by lateral walls 32 and rear wall 33. Member 40 is itself actuated by way of displacement and rotation by means shown in FIG. 6 being located within members 20 and 30. Member 50 includes: a slot being defined by lateral walls 55 and upper wall 51; front facing grooved surface 52; front facing recess or notch 53; and upper convex surface 54. The slot on member 50 and the slot on member 30 accommodate the displacement and rotational motion of member 40. Member 40 is rotatable relative to member 50 within the slot of member 50 while member 50 is rotatable relative to member 60 within the slot of member 60. Member 60 includes: lower convex surface 61; intermediate concave surface 62; lateral flat surface 63 which merges with the surface of member 30; rear facing grooved surface 66; upper convex surface 64; rear facing recess or notch 65; and a slot defined by lateral walls 68. Surface 52 of member 50 and surface 66 of member 60 form a V-shaped pocket or opening in the open configuration and are adapted to accommodate open clip 200.

Clip holder 100 comprises: cylindrical rear portion 110; reduced intermediate portion 120; and front end 130. Portion 110 includes flat rear surface 111. Front end 130 includes slot 121 being defined by rear wall 133 and lateral walls 134 wherein lateral walls 134 are decreasingly spaced apart toward front ends 131 and 132. At front ends 131 and 132, there are provided medial steps to allow placement of open clip 200 onto the medial surfaces of front ends 131 and 132 such that open clip 200 snaps into position as shown being compressed by the medial surfaces of front ends 131 and 132. Clip holder 100 may be held manually at location 135 with the thumb and pointer of one hand while open clip 200 is snapped into place as shown.

Open clip 200 comprises flat straight extension 210 with end 211, flat straight extension 220 with end 221, and curved intermediate portion 230 bridging such extensions. Accordingly, open clip 200 is snapped onto clip holder 100 in a so called reverse fashion wherein the concave side of portion 230 faces clip holder 100.

Therefor, the combination of clip holder 100 and open clip 200 snapped thereon is manually positioned adjacent applicator 10 such that the external surface of extension 210 makes intimate contact with surface 52 of member 50 and the external surface of extension 220 makes intimate contact with surface 66 of member 60. The grooves on surfaces 52 and 66 are just wide enough to accommodate the widths of extensions 210 and 220 to prevent lateral motion of open clip 200. Also, the grooves on surfaces 52 and 66 are just long enough to accommodate the lengths of extensions 210 and 220 such that extension ends 211 and 221 just make contact with the upper surfaces of notches 53 and 65 to prevent upward motion of open clip 200. This therefor defines the position of open clip 200 realtive to applicator 10.

Accordingly, the operation of applicator 10 with snapped on open clip 200 involves placing open clip 200 around the vessel or tissue to be clipped or compressed or strangulated; applying forward motion to member 40 as will be hereinafter explained; thereby causing forward rotation of member 50 relative to member 60; thereby causing closure of clip 200 to the extent necessary or until the internal surfaces of clip extensions 210 and 220 make contact with each other as the case may be; once the vessel or tissue is appropriately clipped, thereafter applying rearward motion to member 40 thereby causing rearward motion of member 50; once member 50 is fully separated from member 60, then closed clip 200 and the vessel or tissue separate from surfaces 52 and 66 to free the closed clip.

FIG. 2 is a top view of the front end of applicator 10 in the open configuration showing member 20, member 30, member 40, member 50, and member 60. Member 50 shows surface 54 and surface 52. Member 60 shows surface 62, surfaces 63, surface 64, and surface 66. Member 40 and member 50 are rotatable relative to each other about horizontal axis A—A while member 40 is rotatable relative to internal rod means not shown herein about axis B—B.

FIG. 3 is a lateral view of the front end of applicator 10 showing member 20, member 30, member 40, member 50, and member 60. Member 50 shows surface 54, notch 53 including upper internal surface 56, and surface 52. Member 60 shows surface 61, surface 62, surface 64, notch 65 including upper internal surface 69, and surface 66. Accordingly, once open clip 200 snaps onto applicator 10 in the open configuration, the external surfaces of clip extensions 210 and 220 are in intimate contact with surfaces 52 and 66 and clip ends 211 and 221 are in intimate contact with surfaces 56 and 69 of of notches 53 and 65 such that lateral and upward motion of open clip 200 is not possible.

FIG. 4 is a bottom view of the front end of applicator 10 in the open configuration showing member 20, member 30, member 40, member 50, and member 60. Member 50 is located within a slot of member 60 being defined by lateral walls 67, rear wall 167, and front wall 267. Member 60 shows surfaces 61. Member 50 rotates relative to member 60 about horizontal axis C—C.

FIG. 5 is a front view of the front end of applicator 10 in the open configuration showing member 30 and member 60. Member 60 shows surfaces 63, surfaces 61, walls 67, and surface 64.

FIG. 6 is a perspective view of the complete applicator 10 in the open configuration showing open clip 200, member 60, member 50, member 40, member 30, member 20, rear hollow tubular member 70, solid cylindrical actuating rod 41, and rear rotatable member 80. Member 60 shows surface 61, surface 62, surface 64, and surface 66. Member 50 shows surface 52, notch 53, and surface 54. Member 70 includes stationary handle portion 72 and curved leaf spring 92. Member 70 is fixedly attached to member 20 at location 71. Member 80 includes rotatable handle 81, upper rotatable extension 82, and curved leaf spring 91. Extension 82 is rotatably attached to the rear end of rod 41 by way of a ball 42 at the end of rod 41 and a vertical slot in extension 82. Handle 81 is rotatable relative to handle 72 about a horizontal axis located at location 94. Spring 91 is fixedly attached to the bottom of handle 81, spring 92 is fixedly attached to the bottom of handle 72, and springs 91 and 92 are rotatably attached to each other at location 93. Accordingly, handles 81 and 72 are manually actuated such that handle 81 is rotated rearwardly towards handle 72, extension 82 is rotated forward thereby causing forwardly longitudinal motion of rod 41, forward motion and variable rotation of member 40 about their common horizontal axis B—B of rod 41 and member 40; then counterclockwise rotation of member 50 about horizontal axis C—C toward member 60, compression of clip 200 onto the vessel or tissue. Thereafter, handle 81 is manually rotated away from handle 72 to reverse the process whereby compressed clip 200 separates from applicator 10 and is released being attached to the vessel or tissue. Springs 91 and 92 apply a biasing force between handles 81 and 72 to help maintain them in the open configuration. It will be apparent that surface 64 and surface 61 facilitate entry of applicator 10 into the tissue; that surface 54 facilitates opening of member 50 within the tissue; and that surface 54 and surface 61 facilitate exit from the tissue.

FIG. 7 is a perspective view of clip holder 100 showing portion 110 with surface 111, portion 120, and portion 130. Portion 130 includes portion 135, ends 131 and 132, and a slot therebetween defined by rear wall 133 and lateral walls 134. The medial surfaces of end portions 131 and 132 include steps 136 for accommodating the lateral edges of open clip curved portion 230 such that clip 200 securely snaps onto holder 100 as in FIG. 1 for transferring open clip 200 as held by holder 100 onto applicator 10 in the open configuration.

FIG. 8 is a perspective view of open clip 200 showing extensions 210 and 220 and respective ends 211 and 221, and curved interconnecting portion 230. Clip 200 may be made of any suitable bendable material such as stainless steel.

In the open configuration, the angle between surfaces 52 and 66 is about 23 degrees; the angle between open clip extensions 210 and 220 is about 23 degrees; the angle between surface 66 and the longitudinal axis of member 30 is about 73 degrees; the angle between surface 52 and the longitudinal axis of member 30 is about 96 degrees; the angle between closed clip extensions 210 and 220 and the longitudinal axis of member 30 in the closed configuration is about 73 degrees; the angle between surface 52 and the longitudinal axis of member 30 in the closed configuration is about 73 degrees; and the angles between the open clip extensions and the longitudinal axis of member 30 in the open configuration are about 73 degrees and about 96 degrees.

While the arrangement according to the present invention has been described in terms of a specific illustrative embodiment, it will be apparent to those skilled in the art that many modifications are possible within the spirit and scope of the disclosed principle.

What is claimed is:

1. A surgical clip applicator system comprising a surgical clip applicator having a front end and a rear end defining a front to rear direction, said surgical clip applicator further comprising:
    a stationary front jaw member including a rear facing grooved surface, a rear facing cancave notch above said rear facing grooved surface and a rear end;
    a rotatable jaw member being located at the rear end of said stationary front jaw member and including a front facing grooved surface and a front facing concave notch above said front facing grooved surface, and rear end; and
    actuating means being located at the rear end of said rotatable jaw member and being connected to said rotatable jaw member about a first horizontal axis being common to said actuating means and to said rotatable jaw member for effecting frontward and rearward rotation of said rotatable jaw member about a second horizontal axis being common to said rotatable jaw member and said stationary front jaw member, such that said rear and front facing grooved surfaces approximate each other when said rotational jaw member is rotated from a fully open configuration to a fully closed configuration relative to said stationary front jaw member; wherein said actuating means includes first and second internal members each having front and rear ends, and a third external member having an upper end and a lower end; said rotatable jaw member being connected to said first internal member front end about said first common horizontal axis and wherein said first member front end exhibits longitudinal motion and rotational motion, said front to rear direction being defined as the longitudinal direction; said second internal member front end being connected to said first internal member rear end about third horizontal axis being common to said second internal member and said first internal member wherein said first internal member rear end and said second internal member front end exhibit longitudinal motion; and said second internal member rear end being connected to said third external member upper end about a fourth horizontal axis being common to said second internal member and said third external member wherein said second internal member rear end exhibits only longitudinal motion and said third external member upper end exhibits rotational motion about a fifth horizontal axis.

2. The surgical clip applicator of claim 1 also further comprising: an external hollow tubular member having a front end and a rear end being located to the rear of said stationary front jaw member wherein the rear end of said stationary front jaw member is fixedly attached to the front end of said external hollow tubular member, said external hollow tubular member accommodating said first and second internal members up to and including said second internal member rear end and said third external member upper end; and a fourth external member having an upper end and a lower end, said external hollow tubular member being fixedly attached at its rear end to said fourth external member upper end and said third external member being rotatable about said fifth horizontal axis being located on said fourth external member.

3. The surgical clip applicator of claim 2 wherein: said third external member lower end is a rotatable handle and wherein said fourth external member lower end is a stationary handle; said surgical clip applicator also further comprising spring means interconnecting said rotatable handle and said stationary handle to maintain said surgical clip applicator in the open configuration.

4. The surgical clip applicator system of claim 1 wherein said notches include upper surfaces, and wherein said surgical clip applicator system also comprises a V-shaped clip, said clip further comprising:
    first and second flat straight extension each including external surfaces and upper and lower ends;
    and a lower curved interconnecting portion including an internal concave surface for interconnecting said first and second extensions;
    said clip being accommodated onto said surgical clip applicator such that:
    said first and second extension external surfaces fit into said front and rear facing surface grooves respectively; and
    said first and second extension upper ends make intimate contact with said front and rear facing notches.

5. The surgical clip applicator system of claim 4 also comprising a clip holder for said clip, said clip lower curved interconnecting portion including lateral edges, said clip holder further comprising:
    a first portion for manually holding said clip holder; and a second portion including two separate ends further including therebetween a slot of decreasing width, said two separate ends each including a medial surface with a step thereon such that the lateral edges of said interconnecting portion are compressively held by said clip holder medial surfaces when the concave surface of said interconnecting portion faces said clip holder first portion; and wherein said clip holder with said clip thereon can be used to snap on said clip onto said surgical clip applicator.

* * * * *